United States Patent
Maywald et al.

(10) Patent No.: US 6,488,818 B1
(45) Date of Patent: Dec. 3, 2002

(54) REMOVAL OF IMPURITIES FROM 3-(2'-ACETOXYETHYL)-DIHYDRO-2(3H) FURANONE

(75) Inventors: Volker Maywald, Ludwigshafen (DE); Horst Hartmann, Böhl-Iggelheim (DE); Norbert Götz, Worms (DE); Gernot Reissenweber, Böhl-Iggelheim (DE); Hartmann König, Heidelberg (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/391,338

(22) Filed: Sep. 8, 1999

(30) Foreign Application Priority Data

Sep. 10, 1998 (DE) .......................................... 198 41 520

(51) Int. Cl.$^7$ ........................... B01D 3/00; C07D 307/33
(52) U.S. Cl. ............................. 203/74; 203/35; 203/43; 203/46; 203/99; 203/DIG. 19; 549/323
(58) Field of Search ................................ 549/323, 322; 203/73, 74, 77, 81, 99, DIG. 19, 35, 57, 43, 46

(56) References Cited

U.S. PATENT DOCUMENTS

| 5,283,326 A | 2/1994 | Hansen et al. | 534/766 |
|---|---|---|---|
| 5,350,863 A | 9/1994 | Kuekenhoehner | 549/323 |
| 5,371,246 A | * 12/1994 | Borchers et al. | 549/425 |
| 5,466,831 A | 11/1995 | Schnurr et al. | 549/323 |
| 6,201,135 B1 | * 3/2001 | Maywald et al. | 549/323 |

FOREIGN PATENT DOCUMENTS

| EP | 0584631 | 3/1994 |
|---|---|---|
| WO | 99/29680 | 6/1999 |

\* cited by examiner

*Primary Examiner*—Virginia Manoharan
(74) *Attorney, Agent, or Firm*—Keil & Weinkauf

(57) ABSTRACT

A process for removing impurities from 3-(2'-acetoxyethyl) dihydro-2(3H)furanone (I), where the 3-(2'-acetoxyethyl) dihydro-2(3H)furanone containing the undesirable impurities is initially prepared in a manner known per se by acetylation of 3-(2'-hydroxyethyl)dihydro-2(3H)furanone and the resulting product is subsequently subjected to a distillation or rectification, includes carrying out the distillation or rectification in a plurality of steps, where high-boiling impurities are removed in a first step, the product which is drawn off via the top is subsequently subjected to at least one further step in which low-boilers and intermediate boilers are drawn off via the top and the desired pure I is obtained as bottom product.

6 Claims, No Drawings

REMOVAL OF IMPURITIES FROM 3-(2'-ACETOXYETHYL)-DIHYDRO-2(3H) FURANONE

The present invention relates to a process for removing undesirable impurities from 3-(2'-acetoxyethyl)dihydro-2 (3H) furanone of the formula I

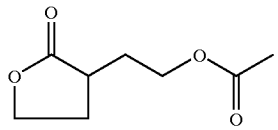

3-(2'-Acetoxyethyl)dihydro-2(3H)furanone is a starting material for preparing methyl tetrahydropyran-4-carboxylate which for its part is an intermediate in the preparation of crop protection agents.

3-(2'-Acetoxyethyl)dihydro-2(3H)furanone is prepared, for example, by processes known per se and described, for example, in U.S. Pat. No. 5,350,863, starting from methyl acetoacetate and ethylene oxide. Another process variant from which 3-(2'-acetoxyethyl)dihydro-2(3H)furanone is obtainable is described in Dokl. Akad. Nauk SSSR 27, 956–959 (1940) and U.S. Pat. No. 5,283,326.

In both variants, the desired 3-(2'-acetoxyethyl)dihydro-2(3H)furanone is formed as a mixture with a number of undesirable byproducts, in particular the isomeric dihydro-3-(2-methyl-1,3-dioxolan-2-yl)-2(3H)-furanone II

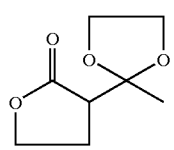

If I which is contaminated in this manner is reacted in a continuous gas phase reaction with methanol in the presence of acidic catalysts to give methyl tetrahydropyran-4-carboxylate, the yields are significantly lower and the operating life of the catalyst is significantly shorter than when a product of high purity without byproducts is employed. This is probably due to the fact that most byproducts contain labile acetal groups which decompose on the surface of the catalyst to give oligomeric and polymeric products.

It is not possible to remove the undesirable byproducts, in particular the isomeric dihydro-3-(2-methyl-1,3-dioxolan-2-yl)-2(3H)furanone II adequately by simple batchwise distillation or rectification. In addition, during the batchwise distillation or rectification of 3-(2'-acetoxyethyl) dihydro-2(3H)furanone I containing the undesirable impurities, other low-boilers and intermediate boilers which are difficult to remove are formed, which recontaminate the purified I obtained in the distillate.

It is an object of the present invention to provide a process for removing undesirable byproducts, in particular II, and also newly formed low-boilers and intermediate boilers from mixtures with I.

We have found that this object is achieved by a process for removing impurities from 3-(2'-acetoxyethyl)dihydro-2 (3H)furanone (I), where the 3-(2'-acetoxyethyl)dihydro-2 (3H)furanone containing the undesirable impurities is initially prepared in a manner known per se by acetylation of 3-(2'-hydroxyethyl)dihydro-2(3H)furanone and the resulting product is subsequently subjected to a distillation or rectification, which comprises carrying out the distillation or rectification in a plurality of steps, where high-boiling impurities are separated off in a first step, the product which is drawn off via the top is subsequently subjected to a further step in which low-boilers and intermediate boilers are drawn off via the top and the desired pure I is obtained as bottom product.

Surprisingly, the process according to the invention affords a significantly higher degree of purity of the desired 3-(2'-acetoxyethyl)dihydro-2(3H)furanone (I) than in the customary sequence in the distillation or rectification where low-boilers and intermediate boilers are removed before the high-boilers and the product of value is drawn off at the top of the column. The reason for this is that, during the removal of the high-boilers, low-boilers and intermediate boilers are formed which can then not be removed in the customary sequence of the steps and which reduce the purity of the top product.

Preferred embodiments of the process according to the invention are shown in the subclaims and the description below.

The process according to the invention starts with the mixture of 3-(2'-acetoxyethyl)dihydro-2(3H)furanone (hereinbelow referred to as I) and undesirable impurities which is obtainable by known processes described in the introduction.

This mixture is generally prepared by acetylation of 3-(2'-hydroxyethyl)dihydro-2(3H)furanone. The preferred acetylating agent is acetic anhydride or acetic acid; however, in principle, all acetylating agents which are known to the person skilled in the art for corresponding acetylations are suitable. In general, the acetylation is carried out at temperatures in the range from 40° C. to 200° C., preferably from 60 to 140° C., over a period of from 0.5 to 10 h, preferably from 0.8 to 5 h and in particular from 1 to 3 h.

To ensure complete acetylation, the acetylating agent is generally employed in a molar excess of from 5 to 50%, preferably from 5 to 20%, based on the 3-(2'-hydroxyethyl) dihydro-2(3H)furanone present in the mixture.

In a first preferred embodiment of the process according to the invention, the acetic acid formed as coproduct during the acetylation is firstly distilled off. By adding a suitable organic solvent and water, a phase separation is then carried out and the organic phase is subsequently extracted. Suitable organic solvents are in particular aromatic hydrocarbons and particularly alkylated benzene derivatives such as xylene or toluene. The organic extracts are combined and the solvent is then removed by a preliminary distillation or rectification step in at least one column, before the multistep distillation of claim 1 is carried out.

In another preferred embodiment of the process according to the invention, the product formed during the acetylation is treated with strong mineral acids before it is subjected to the rectification or distillation. Preferred mineral acids are hydrochloric acid and particularly preferably sulfuric acid. The latter is preferably employed in a strength of at least 80% and especially in the form of concentrated sulfuric acid.

The amount of acid used here can be varied within a wide range; in some cases, it has been found advantageous for the molar ratio of strong mineral acid, based on the amount of acetylating agent employed in the previous step, to be in the range of from 1:20 to 1:3, in particular from 1:15 to 1:7 and especially from 1:8 to 1:12.

During the treatment with the mineral acid, the temperature is generally in a range from 10 to 80° C., preferably from 20 to 60° C. and in particular from 30 to 50° C. The duration of the treatment is generally in the range from 0.3 to 10 h, in particular from 1 to 5 h, but can, in principle, be varied within wide limits.

After the treatment with strong mineral acids, the decomposition products of the undesirable impurities, in particular of dihydro-3-(2-methyl-1,3-dioxolan-2-yl)-2(3H)-furanone II, can be removed in a simple manner. Particularly preferably, after the treatment with the mineral acid, the mineral acid is initially neutralized by addition of a base and the acetic acid formed as coproduct during the acetylation is subsequently, if appropriate, removed as described in the first preferred embodiment. This is then followed by the multistep distillation or rectification of claim 1.

The purity of I after the process according to the invention is generally at least 98% by weight, preferably at least 98.5% by weight and particularly preferably at least 99% by weight.

The I obtainable by the process according to the invention can be reacted in a known manner in high yield and with good catalyst operating life to give methyl tetrahydropyran-4-carboxylate. This is an important intermediate in the preparation of crop protection agents.

EXAMPLE 1

Comparison

In a 1 m³ pressure vessel, a mixture of 282.5 kg (2.44 kmol) of methyl acetoacetate, 340 l (271 kg) of methanol and 30.8 kg (0.17 kmol) of a 30% strength solution of sodium methoxide in methanol was initially charged, and 214.4 kg (4.87 kmol) of ethylene oxide are then pumped in at 60° C. with stirring over a period of 8 hours. The mixture was then stirred at 60° C. for 24 h. The reaction discharge was repeatedly flushed with nitrogen and then transferred into a 1 m³ stirred apparatus fitted with a column. The catalyst was then neutralized by adding 8.5 kg (83.3 mol) of sulfuric acid (96%). The low-boiling components, essentially methanol, methyl acetate and methyl glycol, were distilled off at 10 mbar (1013 Pa) up to a bottom temperature of 100° C. At 100° C., 225.7 kg (2.21 kmol) of acetic anhydride were added with stirring to the distillation residue over a period of 1 hour, and the mixture was then stirred at 100° C. for 2 h. Excess acetic anhydride and the acetic acid formed as coproduct during the acetylation were then distilled off, and the crude discharge was cooled. After addition of 350 kg of toluene and 150 kg of water, the phases were separated and the aqueous phase was extracted twice with in each case 200 kg of toluene. The organic extracts were combined and the solvent was removed under reduced pressure. The residue was rectified batchwise under reduced pressure at 10 mbar (b.p. 161° C./10 mbar). This gave 301.5 kg (72%) of 3-(2'-acetoxyethyl)dihydro-2(3H)furanone (calculated 100%).

| Composition: | |
|---|---|
| 3-(2'-Acetoxyethyl)dihydro-2(3H)furanone: | 95.0% |
| Dihydro-3-(2-methyl-1,3-dioxolan-2-yl)-2(3H)furanone: | 3.5% |
| 3-(2'-Hydroxyethyl)dihydro-2(3H)furanone: | 0.50% |
| Others: | 1.0% |

COMPARATIVE EXAMPLE 2
(Customary Multistep Rectification, Removal of the Product of Value Via the Top)

In a 1 m³ pressure vessel, a mixture of 282.5 kg (2.44 kmol) of methyl acetoacetate, 340 l (271 kg) of methanol and 30.8 kg (0.17 kmol) of a 30% strength solution of sodium methoxide in methanol was initially charged, and 214.4 kg (4.87 kmol) of ethylene oxide are then pumped in at 60° C. with stirring over a period of 8 hours. The mixture was then stirred at 60° C. for 24 h. The reaction discharge was repeatedly flushed with nitrogen and then transferred into a 1 m³ stirred apparatus fitted with a column. The catalyst was then neutralized by adding 8.5 kg (83.3 mol) of sulfuric acid (96%). The low-boiling components, essentially methanol, methyl acetate and methyl glycol, were distilled off at 10 mbar (1013 Pa) up to a bottom temperature of 100° C. At 100° C., 225.7 kg (2.21 kmol) of acetic anhydride were added with stirring to the distillation residue over a period of 1 hour, and the mixture was then stirred at 100° C. for 2 h. Excess acetic anhydride and the acetic acid formed as coproduct during the acetylation were then distilled off, and the crude discharge was cooled. After addition of 350 kg of toluene and 150 kg of water, the phases were separated and the aqueous phase was extracted twice with in each case 200 kg of toluene. The organic extracts were combined, and further worked-up as follows: In a first continuously operated column (diameter: 43 mm, packed with 1 m Sulzer BX packing), the toluene was distilled off at a top vacuum of 300 mbar at a purity of 99.9% by weight, and the toluene-free product of value was drawn off from the bottom. From here, the product of value was transferred into a second continuously operated column (diameter: 43 mm, packed with 2.4 m Sulzer CY packing) where low-boilers and intermediate boilers were removed via the top (top pressure: 10 mbar). The bottom product was freed of high-boilers in a third continuously operated column (diameter: 43 mm, packed with 2.4 m Sulzer CY packing) (top pressure: 10 mbar) and obtained as the top product (b.p. 161° C./10 mbar).

This gave 303.7 kg (72%) of 3-(2'-acetoxyethyl)dihydro-2(3H)furanone (calculated 100%).

| Composition: | |
|---|---|
| 3-(2'-Acetoxyethyl)dihydro-2(3H)furanone: | 98.9% |
| Dihydro-3-(2-methyl-1,3-dioxolan-2-yl)-2(3H)furanone: | 0.1% |
| 3-(2'-Hydroxyethyl)dihydro-2(3H)furanone: | 0.3% |
| Others: | 0.6% |

EXAMPLE 3
(According to the Invention (Three-fold Cont. Rectification, Removal of the Product of Value from the Bottom))

In a 1 m³ pressure vessel, a mixture of 282.5 kg (2.44 kmol) of methyl acetoacetate, 340 l (271 kg) of methanol and 30.8 kg (0.17 kmol) of a 30% strength solution of sodium methoxide in methanol is initially charged, and 214.4 kg (4.87 kmol) of ethylene oxide are then pumped in at 60° C. with stirring over a period of 8 hours. The mixture was then stirred at 60° C. for 24 h. The reaction discharge was repeatedly flushed with nitrogen and then transferred into a 1 m³ stirred apparatus fitted with a column. The catalyst was then neutralized by adding 8.5 kg (83.3 mol) of sulfuric acid (96%). The low-boiling components, essentially methanol, methyl acetate and methyl glycol, were distilled off at 10 mbar up to a bottom temperature of 100° C. At 100° C., 225.7 kg (2.21 kmol) of acetic anhydride were added with stirring to the distillation residue over a period of 1 hour, and the mixture was then stirred at 100° C. for 2 h. Excess acetic anhydride and the acetic acid formed as coproduct during the acetylation were subsequently distilled off, and the crude discharge was cooled. After addition of 350 kg of toluene and 150 kg of water, the phases were separated and the aqueous phase was extracted twice with in each case 200 kg of toluene. The organic extracts were combined, and further worked-up as follows: In a first continuous column (diameter: 43 mm, packed with 1 m Sulzer BX packing), the toluene was distilled off at a top vacuum of 300 mbar at a purity of 99.9% by weight, and the toluene-free product of value was drawn off from the bottom. From here, the product of value was transferred into a second continuous column (diameter: 43 mm, packed with 2.4 m Sulzer CY packing), where high-boilers were removed (top pressure: 10 mbar). The top product was then freed of low-boilers and intermediate boilers in a third continuous column (diameter: 43 mm, packed with 2.4 m Sulzer CY packing) (top pressure: 10 mbar) and obtained from the bottom of the column (b.p. 161° C./10 mbar).

This gave 304,5 kg (73%) of 3-(2'-acetoxyethyl)dihydro-2(3H)furanone (calculated 100%)

| Composition: | |
|---|---|
| 3-(2'-Acetoxyethyl)dihydro-2(3H)furanone: | 99.5% |
| Dihydro-3-(2-methyl-1,3-dioxolan-2-yl)-2(3H)furanone: | <0.1% |
| 3-(2'-Hydroxyethyl)dihydro-2(3H)furanone: | 0.3% |
| Others: | 0.1% |

To examine the effect of the degree of purity of I on the subsequent reaction, the products obtained from Examples 1 to 3 were reacted to give methyl tetrahydropyran-4-carboxylate according to the following general equation:

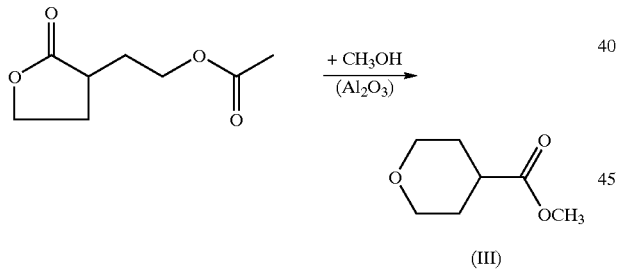

(III)

Per hour, a solution comprising 172 g of 3-(2'-acetoxyethyl)dihydro-2(3H)furanone and 192 g of methanol was evaporated and, in a tubular reactor at 250° C., passed over 2000 g of a γ-aluminum oxide catalyst (Pural SB™, formed into 2 mm extrudates, dried at 120° C./16 h and calcined at 520° C./3 h). The gaseous reaction discharge was condensed and the resulting tetrahydropyran-4-carboxylic ester was purified by batchwise distillation (b.p. 117° C./30 mbar)

The results of the reactions of 3-(2'-acetoxyethyl)dihydro-2(3H)furanone I with varying proportions of dihydro-3-(2-methyl-1,3-dioxolan-2-yl)-2(3H)-furanone II are summarized in Table 1 (in all cases conversion was 100%):

TABLE 1

| Proportion of II in % | Purity of I in % | Yield of III at the beginning | Yield of III after 60 h | Yield of III after 1200 h | Yield of III after 1440 h |
|---|---|---|---|---|---|
| 3.5 (Ex. 1) | 95.0 | 55% | 39% | — | — |
| 0.1 (Ex. 2) | 98.9 | 68% | 68% | 68% | 62% |
| <0.1 (Ex, 3) | 99.5 | 68% | 68% | 68% | 68% |

The results in the above table show the pronounced effect of the content of impurities, in particular II, on the further processing of I.

We claim:
1. In a process for isolating 3-(2'-acetoxyethyl)dihydro-2(3H)furanone (I) from a reaction mixture obtained by acetylating 3-(2'-hydroxyethyl)dihydro-2(3H)furanone, the improvement which consists essentially of isolating the 3-(2'-acetoxyethyl)dihydro-2(3H)furanone (I) by means of a plurality of distillation or rectification steps, wherein the reaction mixture, prior to an initial distillation, is either
i) first subjected to a preliminary distillation or rectification to remove acetic acid which is formed as a coproduct in the acetylation, and is subsequently extracted with an organic solvent, and the resulting organic extract is introduced into the initial distillation or rectification step, or
ii) first treated with a strong mineral acid;
in the initial distillation or rectification step, the reaction mixture is separated into a first fraction comprising the 3-(2'-acetoxyethyl)dihydro-2(3H)furanone (I) and constituents which have a boiling point lower than (I) which first fraction is recovered over the top, and a second fraction comprising constituents which have a boiling point higher than (I) which is recovered as a bottom residue of the initial distillation or rectification, and
in a subsequent distillation or rectification step, the first fraction obtained in the initial step is separated into a low-boiler fraction of constituents which have a boiling point lower than (I) which low-boiler fraction is recovered over the top, and a bottom fraction consisting of 3-(2'-acetoxyethyl)dihydro-2(3H)furanone (I) having a purity of at least 99% by weight.
2. The process of claim 1, wherein the strong mineral acid is sulfuric acid.
3. The process of claim 2, wherein the reaction mixture is treated with sulfuric acid at a temperature of from 20 to 70° C.
4. The process of claim 1, wherein the reaction mixture, prior to the initial distillation of rectification, is first treated with the strong mineral acid, and subsequently subjected to the preliminary distillation or rectification, extracted with the organic solvent, and the resulting organic extract is then introduced into the initial distillation or rectification step.
5. The process of claim 4, wherein the strong mineral acid is sulfuric acid.
6. The process of claim 5, wherein the reaction mixture is treated with sulfuric acid at a temperature of from 20 to 70° C.

* * * * *